United States Patent
Thompson et al.

(12)

(10) Patent No.: US 6,212,791 B1
(45) Date of Patent: Apr. 10, 2001

(54) METHOD OF APPLYING INDICIA TO A FAST-DISSOLVING DOSAGE FORM

(75) Inventors: Andrew R. Thompson, Swindon; Richard J. Yarwood, Collingbourne Kingston; Patrick Kearney, Swindon, all of (GB)

(73) Assignee: R.P. Scherer Corporation, Paradise Valley, NV (US)

( * ) Notice: Subject to any disclaimer, the term of this patent is extended or adjusted under 35 U.S.C. 154(b) by 0 days.

(21) Appl. No.: 09/541,156

(22) Filed: Mar. 31, 2000

Related U.S. Application Data

(63) Continuation-in-part of application No. 08/619,478, filed as application No. PCT/US94/10831 on Sep. 26, 1994, now abandoned, and a continuation-in-part of application No. 08/104,486, filed on Oct. 1, 1993, now Pat. No. 5,457,895.

(51) Int. Cl.[7] ............................................. F26B 5/06
(52) U.S. Cl. ........................... 34/296; 34/297; 206/532
(58) Field of Search ....................... 34/284, 287, 289, 34/293, 296, 297; 156/69, 80, 292; 206/532, 484, 538, 28

(56) References Cited

U.S. PATENT DOCUMENTS

| | | | |
|---|---|---|---|
| 510,453 | * 12/1893 | Tobin . | |
| 2,645,852 | * 7/1953 | Weinberg . | |
| 3,125,490 | * 3/1964 | Hershberg | 167/82 |
| 3,534,440 | 10/1970 | Roberts | 18/16 |
| 4,305,502 | * 12/1981 | Gregory et al. | 206/532 |
| 4,754,874 | 7/1988 | Haney | 206/77.1 |
| 5,039,540 | * 8/1991 | Ecanow | 426/385 |
| 5,079,018 | * 1/1992 | Ecanow | 426/385 |
| 5,120,549 | 6/1992 | Gole et al. | 424/484 |
| 5,215,756 | * 6/1993 | Gole et al. | 424/484 |
| 5,298,261 | * 3/1994 | Pebley et al. | 424/488 |
| 5,358,118 | 10/1994 | Thompson et al. | 206/538 |
| 5,457,895 | * 10/1995 | Thompson et al. | 34/296 |
| 5,631,023 | * 5/1997 | Kearney et al. | 424/465 |

OTHER PUBLICATIONS

Method of Applying an Indkia to Fast—Dissolving Dosage Form, Apr. 1995, World Intellectual Property org.
Intraorally Disinterating Preparation and Method for Making it, Jul. 1993, World Intellectual Property org.

* cited by examiner

*Primary Examiner*—Pamela Wilson
(74) *Attorney, Agent, or Firm*—Donald O. Nickey; Andrew G. Rozycki

(57) ABSTRACT

The invention permits the application of an identifying mark onto a fast-dissolving dosage form without the need for application of pressure or printing directly onto the dosage unit. The invention comprises preparing of a fast-dissolving dosage unit that is embossed with an identifying mark such as a manufacturer's logo, medicinal component strength, or other information relating to the unit. The desired identifying mark is first embossed onto the base of the container such as a blister pocket. Liquid suspension is then filled into the container and solidified, e.g., freeze-dried, therein. The resulting dosage unit in the container is thereby embossed with a substantial copy of the identifying mark that was embossed on the base of the container. The embossed identifying mark on the base of the container remains thereon as well thereby affording the ability to learn the identifying mark on the enclosed unit without opening the packet.

18 Claims, 2 Drawing Sheets

METHOD OF APPLYING INDICIA TO A FAST-DISSOLVING DOSAGE FORM

CROSS-REFERENCE TO RELATED APPLICATION

The present application is a continuation-in-part application based on Ser. No. 08/619,478 filed on May 20, 1996, now abandoned, which is based on International Patent Application No. PCT/US94/10831 Sep. 26, 1994, which is a continuation-in-part application of Ser. No. 08/104,486 filed Oct. 1, 1993, now U.S. Pat. No. 5,457,895 issued on Oct. 17, 1995.

FIELD OF THE INVENTION

The present invention relates generally to the identification of dosage forms. More particularly, the present invention relates to the application of indicia to a fast-dissolving dosage form.

BACKGROUND OF THE INVENTION

Medication in forms such as tablets, capsules, caplets, or fast-dissolving dosage forms have been typically packaged in blister packages or sheets of multiple blister pockets or compartments. A base sheet of transparent or opaque plastic, for instance polyvinyl chloride (PVC or PVC-type laminates), will frequently have a plurality of blister pockets projecting from one face thereof, for containing the unit dosages of medication.

If the units of medication to be packaged in the blister package are solid units such as tablets, capsules, or caplets, the solid units may simply be deposited into the blister pockets of the base sheet. On the other hand, if the units to be packaged are freeze-dried, fast-dissolving dosage forms (FDDF), the medication may be dosed and frozen directly within the blister pockets and then dried therein using a freeze-drying process, as explained by Gregory et al., U.S. Pat. No. 4,305,502. The freeze-drying process is well known in the art and may involve first dosing a liquid suspension into the preformed blister pockets of a base sheet. The base sheet containing the suspension is then cooled by a medium such as liquid nitrogen or carbon dioxide, thereby freezing the contents of the blister pockets. The frozen contents may then be subjected to reduced pressure to complete the freeze drying process.

Various techniques which can utilize preformed pockets (such as blister pockets) to create fast-dissolving dosage forms are described in (i) U.S. Pat. Nos. 5,120,549 and 5,215,756 (hereinafter referred to as the "Gole Process"); (ii) U.S. Pat. No. 5,298,261 (hereinafter the "Pebley Process"); and (iii) U.S. Pat. Nos. 5,039,540 and 5,079,018 (hereinafter the "Ecanow Process"), the entire teachings of which are herein incorporated by reference. Another technique is described in PCT Application No. JP 92/01631 filed Dec. 12, 1992 and published as International Publication No. WO 93/12769 (referred to as the "Yamanouchi Process"), the entire teaching of which is incorporated herein by reference. Each of the references disclose techniques to create a fast-dissolving dosage which is at least formed (in contrast to fully processed) in a pocket.

In broad terms, the Gole Process describes a dosage form using a solid-state dissolution method whereby a delivery matrix and first solvent are solidified and subjected to a second solvent at a temperature which permits the removal of the first solvent while leaving the matrix as the product.

The Pebley Process discloses a method of preparing a rapidly disintegrating tablet involving vacuum drying the unbound liquid from a matrix at a temperature above the collapse temperature (i.e., initial matrix melting point) during primary drying, thereby evaporating the free solvent through solid to liquid to gas phases (as opposed to conventional lyophilization which removes solvent directly from solid to gas).

The Ecanow Process discloses a method of preparing freeze-dried readily dissolvable formulations by combining a hydrated gel or foam together with a rigidifying agent and subsequently dehydrated with an anhydrous organic liquid desiccant at about 0° C.

The Yamanouchi Process discloses intraorally disintegrating solid preparations prepared by combining the active ingredient with a sugar (such as lactose and/or mannitol) and agar. The dosage forms are then dried under decreased pressure or forced air conditions.

The pharmaceutical industry abounds with a variety of dosage forms, many of which are very similar, if not identical to each other in outward appearance. It is therefore often necessary to place an identifying logo, code, or other mark on each individual dosage form. Such mark might identify the manufacturer, the brand name, the active component strength or any other useful information regarding the dosage form. Further, several states in the United States currently require certain identifying markings to appear on individual units of medication.

Solid units of medication such as tablets, capsules or caplets have been acceptably identified by printing information directly onto the unit. Alternatively, solid units have been embossed with an identifying mark by compressing an embossment into the surface of the unit. The latter method is illustrated by or analogous to the processes disclosed by Roberts in U.S. Pat. No. 3,534,440; Weinberg in U.S. Pat. No. 2,645,852; and Tobin in U.S. Pat. No. 510,453, which disclose direct pressing techniques to emboss various articles.

While such methods are well suited to the application of an identifying mark to most solid units of medication, such methods are not well-suited for the application of identifying marks to fast-dissolving units. In particular, the application of compression techniques would cause deformation, reduced porosity and increased dispersion time, as well as possibly cracking the fast-dissolving dosage forms due to their inherent fragility, surface undulation, moisture sensitivity and chemical makeup. Similarly, the chemical makeup, moisture sensitivity, porosity and surface undulation of fast-dissolving dosage forms would cause ink to dissolve the dosage forms at the point of contact or to diffuse throughout the dosage forms leading to clarity problems.

Therefore, the need exists for improved products and methods of manufacturing relating to fast-dissolving dosage forms and embossing them without adversely affecting the structural or chemical properties thereof.

SUMMARY OF THE INVENTION

The present invention provides a method for applying indicia to fast-dissolving dosage forms directly during the dosage-forming process. In particular, a desired logo or other product information is first embossed or otherwise formed into the base of a dosage pocket or blister in which the unit will be formed, and an appropriate dose of a medicated liquid suspension is deposited into the embossed pocket. The process of forming the dosage is then initiated and the embossment on the base of the pocket is copied to the adjacent base of the dosage form.

The invention includes a fast-dissolving dosage form bearing an embossed identifying mark prepared according to the method of the invention. The invention also provides for a combination including an embossed blister pocket together with an embossed fast-dissolving dosage form contained therein.

Among the advantages of the invention is that it provides a product and method which apply indicia to fast-dissolving dosage forms which preserve the structural, chemical and delivery advantages and avoid cracking or otherwise deforming or dissolving the dosage form. Yet another advantage of the invention is that it is a low cost method of manufacturing of a properly marked, fast-dissolving dosage form.

Thus there is disclosed, a method for applying an identifying mark to a fast-dissolving dosage form which comprises forming a blister pocket having at least one generally continuous blister pocket surface bearing an identifying embossment, which is discernible from the generally continuous blister surface and which represents a dosage identifying mark and forming the fast-dissolving dosage form directly into the blister pocket so that the fast dissolving dosage form includes a generally continuous dosage surface corresponding to the blister pocket surface and tactile embossed identifying mark thereon corresponding to the identifying embossment wherein forming the fast-dissolving dosage form comprises a process selected from the group consisting of a solid-state dissolution process, a vacuum drying process above collapse temperature, a hydrated gel or foam desiccation process and a sugar admixture and drying process.

There is further disclosed a combination comprising a blister pocket having a generally continuous blister pocket surface embossed with an identifying embossment, and a fast-dissolving dosage form contained in the blister pocket having a generally continuous dosage surface bearing a tactile embossed identifying mark corresponding to the identifying embossment on the blister pocket, wherein the tactile embossed identifying mark is applied to the generally continuous dosage surface.

BRIEF DESCRIPTION OF THE DRAWINGS

There is shown in the attached drawings, a preferred embodiment of the present invention, the numerical references remaining constant throughout the drawings.

DETAILED DESCRIPTION OF THE INVENTION

A preferred embodiment of the invention is described herein with reference to a fast-dissolving dosage unit produced by a forming process in the pockets of a blister pack.

Figure 1:
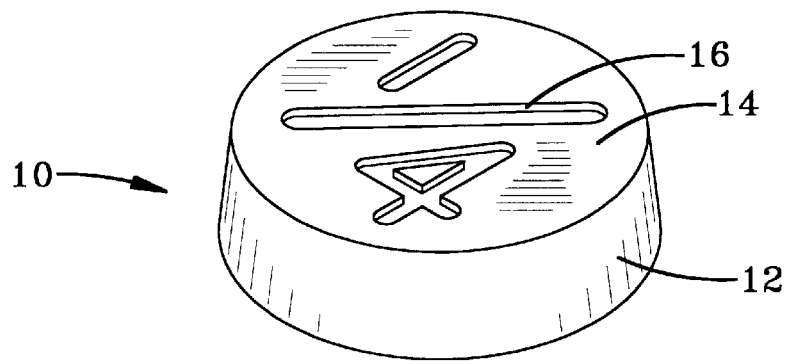
FIG. 1 is a perspective view showing an embossed, fast-dissolving dosage unit made in accordance with the present invention.

FIG. 1 is a perspective view showing an embossed dosage unit 10 made in accordance with the present invention. The dosage unit 10 comprises a body 12 and a base 14. For illustrative purposes, unit 10 is shown with its base 14 on the top. The base 14 of the unit is embossed with an identifying mark or embossment 16. While FIG. 1 illustrates the embossment of the identifying mark "¼" on the base of the unit, the present invention is not limited to this or any other particular choice of identifying mark. In the preferred embodiment, the dosage unit of the present invention can be embossed with any desired identifying mark 16. For instance, it may be useful to prepare freeze-dried pharmaceutical tablets that are embossed with a manufacturer's logo, brand name, component strength or any other information regarding the tablet. The embossment 16 can comprise a marking that either protrudes outwardly from the surface of the base 14 or protrudes inwardly from the surface of the base 14 (creating an elevated or depressed identifying mark on the unit), or a combination of both outward and inward protrusions. The invention is not limited to a particular type of embossment.

Figure 2:
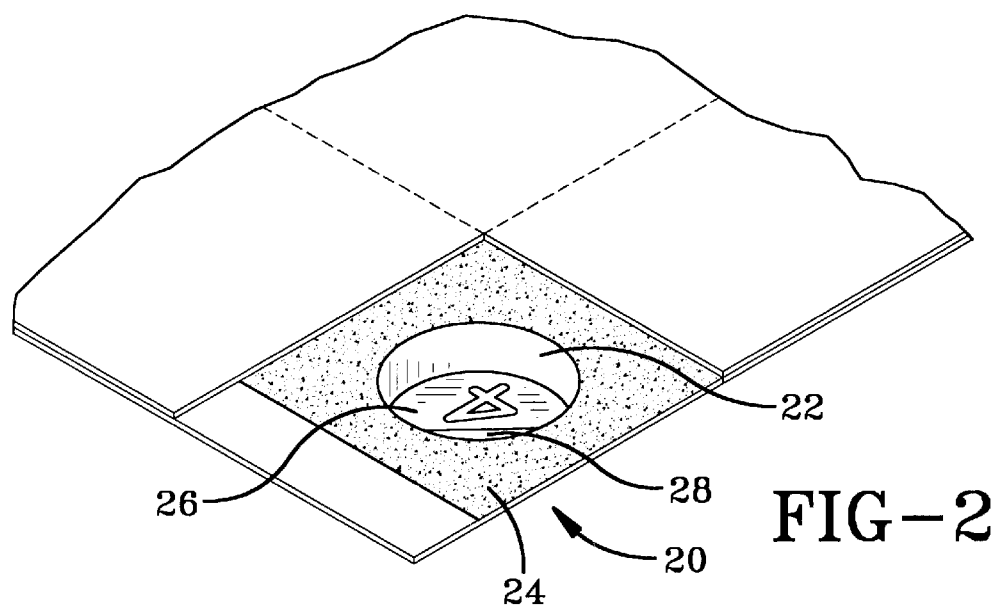
FIG. 2 is a perspective top view showing a portion of a blister package having at least one embossed blister pocket.

FIG. 2 illustrates a perspective top view of a portion of a blister package 20. Illustrated in particular is an embossed blister pocket 22 recessed in the blister package 20. The blister pocket 22 can be one of a plurality of such pockets arranged in the blister package 20. The blister package 20 accordingly comprises a blister sheet 24 and at least one recessed blister pocket 22. The interior surface or base 26 of the blister pocket 22 is embossed with an identifying mark or embossment 28. The embossment on the base 26 of the blister pocket is substantially the reverse of the desired embossment 16 on the base 14 of the dosage unit 10. While, in the preferred embodiment, the embossment 28 is formed on the base of the blister pocket, the present invention contemplates one or more embossed identifying marks formed on any of the interior surfaces of the blister pocket.

Figure 3:
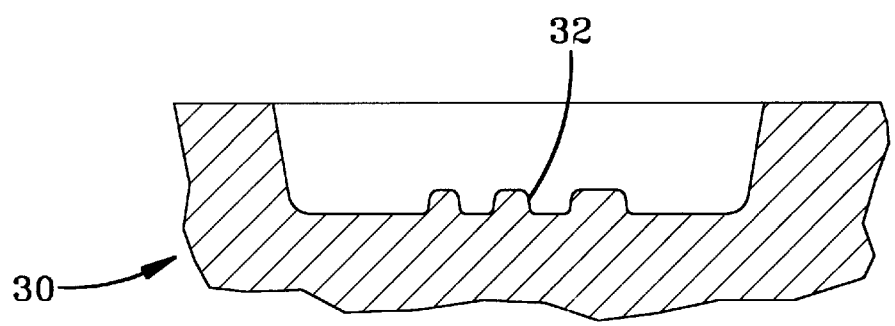
FIG. 3 is a side elevational view of a portion of a machine tool bearing a code to be embossed to a plastic blister pocket web during a thermoforming process in accordance with the present invention.
Figure 4:
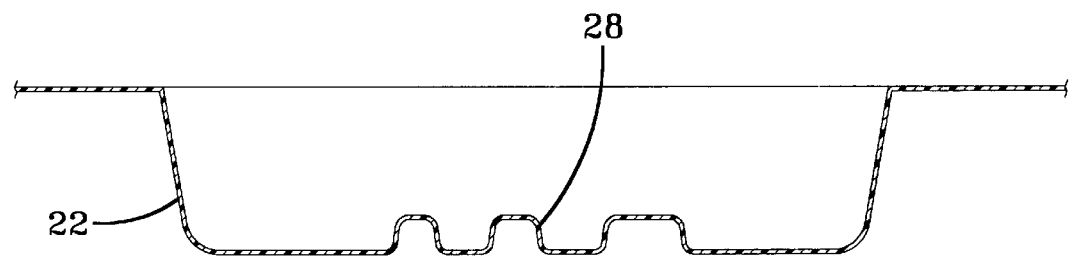
FIG. 4 is a side elevational view of an embossed blister pocket thermoformed in the machine tool of FIG. 3.

FIGS. 3 and 4 illustrate in part the thermoforming of an embossed blister pocket in accordance with the present invention. FIG. 3 illustrates a side elevational view of a machine tool 30 bearing a raised (or lowered) identifying mark 32. The machine tool 30 is used to thermoform by known processes an embossed blister pocket 22, an example of which is illustrated by the side elevational view of FIG. 4. The raised identifying mark 32 on the machine tool 30 is thereby substantially identical to the embossed identifying mark 28 on the base of the blister pocket 22.

Figure 5:
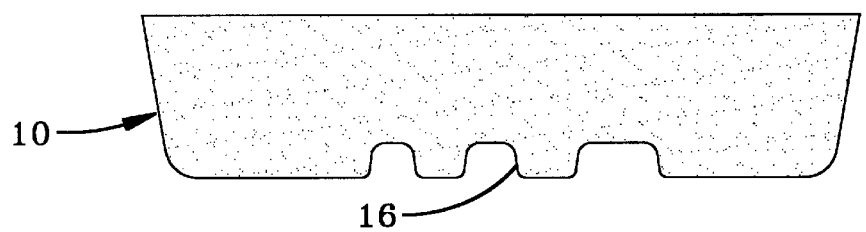
FIG. 5 is a side elevational view of an embossed dosage form prepared in the embossed blister pocket of FIG. 4.

FIG. 5 illustrates the side elevational view of a dosage unit 10 formed in the embossed blister pocket 22 in accordance with the present invention. The dosage unit can be prepared using the well-known process of forming a fast-dissolving dosage form as disclosed by Gregory et al. in U.S. Pat. No. 4,305,502. For instance, the process can comprise first dosing aliquots of liquid suspension containing active medicament directly into the embossed blister pocket 22. At least a portion of the liquid suspension is thereby in contact with the embossed identifying mark 28 on the base 26 of the blister pocket. The blister pocket 22 or the entire blister package 20 containing the liquid suspension is then cooled by application of a medium such as liquid nitrogen or carbon dioxide, thereby freezing the contents of the blister pocket. Finally, the frozen contents are preferably subjected to reduced pressure to complete the freeze-drying process. The result is a porous freeze-dried unit 10 having an embossment 16 that coincides substantially with the embossment 28 on the base 26 of the blister pocket 22, the porous freeze-dried unit being contained within the embossed blister pocket.

Forming fast-dissolving dosage forms can be accomplished using various other methods and techniques. For example, fast-dissolving dosage forms can be prepared and deposited into blister pockets using the methods disclosed in the Cole Process, the Pebley Process, the Ecanow Process and the Yamanouchi Process. Each of the references disclose techniques to create fast-dissolving dosage forms which are at least formed (in contrast to fully processed) in a pocket. Accordingly, forming the fast-dissolving dosage form can comprise a process selected from the group consisting of a solid-state dissolution process, a vacuum drying process above collapse temperature, a hydrated gel or foam desiccation process, and a sugar admixture and drying process.

The Gole Process discloses a dosage form using a solid-state dissolution preparation method whereby a delivery matrix and first solvent are solidified and subjected to a second solvent at a temperature which permits the removal of the first solvent while leaving the matrix and second solvent as the product. More specifically, one or more delivery matrix forming agents (and optionally an active agent) are dissolved or dispersed in a first solvent, solidified, and contacted with a second solvent at a temperature at or higher than the solidification point of the second solvent and at a temperature at or lower than the solidification point of the first solvent. The first solvent in the solidified state is substantially miscible with the second solvent, while the matrix forming agent(s) are substantially insoluble in the second solvent. The first solvent is then removed from the solidified matrix yielding a solid matrix, free from the first solvent.

Fast-dissolving forms made in accordance with the Gole Process exhibit uniform high porosity while having sufficient strength, i.e., resistance to disintegration or crumbling under normal manufacturing and handling conditions.

The Pebley Process discloses a method of preparing a rapidly disintegrating tablet involving vacuum drying the unbound liquid from a matrix at a temperature above collapse temperature (i.e., initial matrix melting point) during primary drying, thereby evaporating the free solvent through solid to liquid to gas phases (as opposed to conventional lyophilization which removes solvent directly from solid to gas). In particular, a mixture is prepared including sufficient amounts of water, gum and a carbohydrate to form a rapidly dissolving tablet. The mixture is formed into the desired shape, frozen below its collapse temperature (preferably below the equilibrium freezing temperature of the mixture) to form the tablet.

Dosage forms prepared according to the Pebley Process have a lower porosity and higher density than conventional freeze-dried products, reduced fragility and are less likely to be broken by mechanical forces exerted on the tablet.

The Ecanow Process discloses a method of preparing freeze-dried readily dissolvable formulations by combining a hydrated gel or foam together with a rigidifying agent and subsequently dehydrated with an anhydrous organic liquid desiccant at about 0° C. In particular, a composition of a hydrated gel or foam material and a rigidifying agent for the gel or foam are intimately contacted with an anhydrous organic liquid desiccant such as anhydrous ethyl alcohol at a temperature of about 0° C. or below until substantially all of the water is removed from the gel or foam material.

The dosage forms prepared according to the Ecanow Process overcome objectionable tastes of incorporated nutrients and drugs, retain the characteristics of a stable suspension when they disintegrate orally or in liquids, and the active ingredients are readily absorbed.

The Yamanouchi Process discloses intraorally disintegrating solid preparations prepared by combining the active ingredient with a sugar such as lactose and/or mannitol, and agar in proportions relative to the solid component and drying after setting under decreased pressure or forced air conditions. Specifically, the Yamanouchi process involves initially suspending the active ingredient and sugar comprising lactose and/or mannitol in 40–60% w/w, relative to the weight of the solid components, of an agar aqueous solution of a concentration of 0.3–2.0% w/w, filling into molds, and drying after setting in the form of jelly. Drying can be performed by drying at decreased pressure or forced air drying.

According to the Yamanouchi Process, the dosage forms prepared by such method disintegrate rapidly in the oral cavity and are sufficiently strong to be handled so that they can be used in convenient packaging and can be easily distributed, carried and handled after removal from packaging.

Blister package components typically include a base with pockets and a removable or breakable laminate layer sealing the dosage unit within the pocket. Materials which can be used to produce the base include those materials well-known and readily available in the art. For example, PVC and PVC derivatives can be used for the base material. The laminate layer can be composed of materials well-known and readily available in the art as well, such as plastics and aluminum, for example.

It will be understood by those skilled in the art that the present invention is not limited to the use of embossed blister pockets or blister packaging to prepare the embossed freeze-dried units. Various other embossed or embossable containers may be used as well. Further, the dosage unit can be formed into a variety of shapes and sizes based upon the shape and size of the container pockets used in the formation process.

Figure 6:
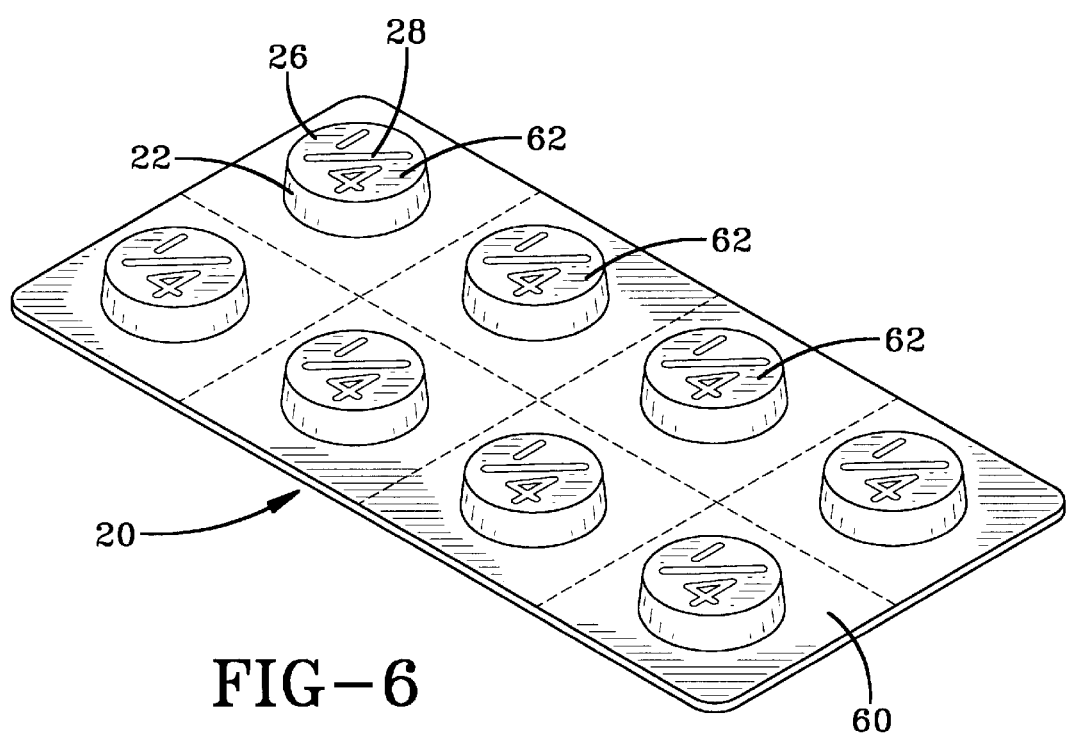
FIG. 6 is a perspective view of the base of a blister package showing the embossments that are copied to the enclosed dosage forms.

Finally, FIG. 6 illustrates an added advantage of the present invention. Shown in FIG. 6 is a perspective view of the bottom surface 60 of a blister package 20 containing embossed dosage units in accordance with the present invention. Projecting from the bottom surface of the blister package is the exterior surface 62 of a plurality of blister pockets 22. Pursuant to the present invention, the base 26 of each blister pocket 22 has been embossed with an identifying mark 28 that is substantially identical to the identifying marks 16 embossed on each respective enclosed unit 10. Thus, the identifying mark is visible both on the given unit as on the exterior surface of the blister pocket in which the unit is contained. This feature can be used to provide useful information to assist in the proper dispensing of pharmaceuticals without the need for first opening the blister package containing the pharmaceutical.

While the invention has been described in the specification with reference to particular details, it will be appreciated by those skilled in the art that various modifications, substitutions, changes can be made without departing from the spirit and scope of the invention.

We claim:

1. A method for applying an identifying mark to a fast-dissolving dosage form comprising:

forming a blister pocket having at least one generally continuous blister pocket surface bearing an identifying embossment, said identifying embossment being discernible from said generally continuous blister pocket surface and representing a dosage identifying mark; and forming said fast-dissolving dosage form directly in said blister pocket such that said fast-dissolving dosage form includes a generally continuous dosage surface corresponding to said generally continuous blister pocket surface and tactile embossed identifying mark thereon corresponding to said identifying embossment, wherein forming said fast-dissolving dosage form comprises a process selected from the group consisting of a solid-state dissolution process, a vacuum drying process above collapse temperature, a hydrated gel or foam desiccation process and a sugar admixture and drying process.

2. The method according to claim 1, wherein forming said fast-dissolving dosage form comprises a solid-state dissolution process.

3. The method according to claim 2 wherein the solid-state dissolution process comprises the Gole Process.

4. The method according to claim 1, wherein forming said fast-dissolving dosage form comprises a vacuum drying process above collapse temperature.

5. The method according to claim 4, wherein the vacuum drying process above collapse temperature comprises the Pebley Process.

6. The method according to claim 1, wherein forming said fast-dissolving dosage form comprises a hydrated gel or foam desiccation process.

7. The method according to claim 6, wherein the hydrated gel or foam desiccation process comprises the Ecanow Process.

8. The method according to claim 1, wherein forming said fast-dissolving dosage form comprises a sugar admixture and drying process.

9. The method according to claim 8, wherein the sugar admixture and drying process comprises the Yamanouchi Process.

10. The method according to claim 1, wherein said tactile embossed identifying mark is an elevated identifying mark.

11. The method according to claim 1, wherein said tactile embossed identifying mark is a depressed identifying mark.

12. The method according to claim 1, wherein the step of forming said blister pocket comprises thermoforming.

13. The method according to claim 1, wherein the step of forming said blister pocket comprises cold-forming.

14. The method according to claim 1, wherein said blister pocket comprises aluminum laminate.

15. The method according to claim 1, wherein said blister pocket comprises plastic laminate.

16. The method according to claim 1, wherein said dosage identifying mark comprises indicia of component strength of said fast-dissolving dosage form.

17. The method according to claim 1, wherein said dosage identifying mark comprises indicia of a manufacturer of said fast-dissolving dosage form.

18. A fast-dissolving dosage form bearing an embossed identifying mark applied by the process of claim 1.

* * * * *